United States Patent [19]
Selzer

[11] Patent Number: 5,375,265
[45] Date of Patent: Dec. 27, 1994

[54] HOLDING MEANS

[75] Inventor: Klaus Selzer, Wiehl, Germany

[73] Assignees: Karl-Heinz Müller; Klaus Müller; Peter Müller, Wiehl-Drabenderhohe, Germany

[21] Appl. No.: 872,168

[22] Filed: Apr. 22, 1992

[30] Foreign Application Priority Data

Apr. 22, 1991 [DE] Germany ............... 4113133

[51] Int. Cl.⁵ ............ A41D 17/02; A41D 27/00; A61F 5/44
[52] U.S. Cl. ............................ 2/242; 2/22; 2/59; 2/243.1; 2/114; 66/178 R; 66/178 A; 66/171; 604/345; 604/349
[58] Field of Search ............ 2/16, 22, 59, 60, 239, 2/242, 409, 402, 403, 406, 407, 400, 162, 170, 243.1; 66/175, 177, 178 R, 181; 604/345, 349, 353; 128/761

[56] References Cited

U.S. PATENT DOCUMENTS

| | | | |
|---|---|---|---|
| 963,864 | 7/1910 | Carter | 2/59 X |
| 2,105,758 | 1/1938 | Scarborough | 66/178 R |
| 2,908,982 | 10/1959 | Corley | 2/247 |
| 3,490,072 | 1/1970 | Keltner | 2/114 |
| 3,491,375 | 1/1970 | Beard et al. | 2/402 |
| 3,547,123 | 12/1970 | Sachs | 604/353 |
| 3,648,699 | 3/1972 | Anderson et al. | |
| 4,106,514 | 8/1978 | Lowth | 2/409 X |
| 4,511,358 | 4/1985 | Johnson, Jr. et al. | 604/353 X |
| 4,625,340 | 12/1986 | Hernandez | 2/247 |
| 4,718,124 | 1/1988 | Sawicki et al. | 2/DIG. 7 X |
| 4,752,972 | 6/1988 | Neckerman et al. | 2/DIG. 7 X |
| 5,032,118 | 7/1991 | Mason | |
| 5,048,512 | 9/1991 | Turner et al. | 604/345 X |
| 5,052,058 | 10/1991 | Mueller | 66/177 X |
| 5,131,100 | 7/1992 | Atwater et al. | 66/177 X |

FOREIGN PATENT DOCUMENTS

| | | |
|---|---|---|
| 2917583 | 11/1982 | Germany . |
| 3241517 | 2/1984 | Germany . |
| 662725 | 10/1987 | Switzerland . |

Primary Examiner—Jeanette E. Chapman
Attorney, Agent, or Firm—Harness, Dickey & Pierce

[57] ABSTRACT

A holding apparatus for holding a urine bag on a user's leg, especially the thigh, has a first knitted hose part, a second knitted hose part of the same diameter which is connected to the first hose part via a continuous connecting region. The first hose part is positioned onto a leg. The second hose part is folded upwardly onto the first knitted hose part to secure the urine bag on the leg. Also, a separating region, in the connecting region, enables the passage of an outlet of the urine bag when the knitted hose parts are in a folded condition.

11 Claims, 2 Drawing Sheets

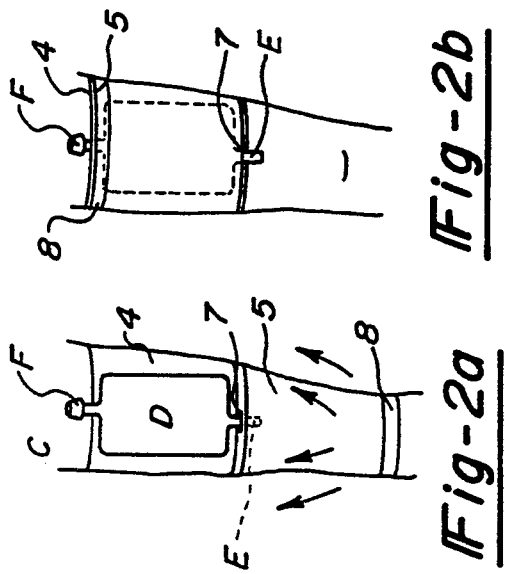
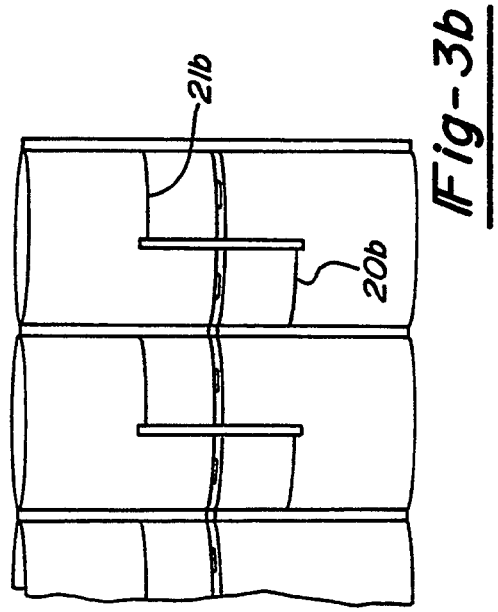
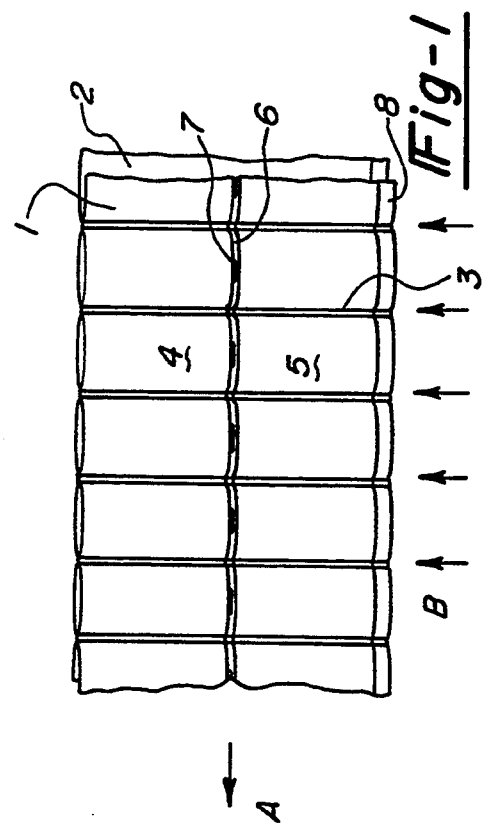
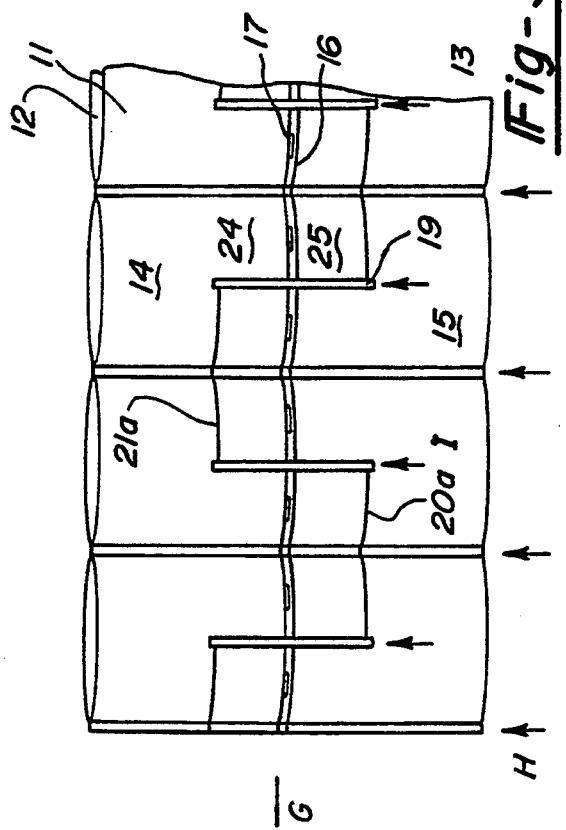

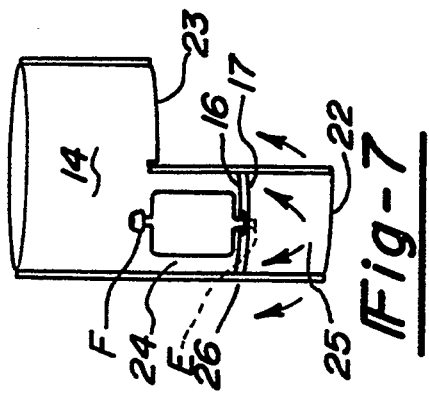
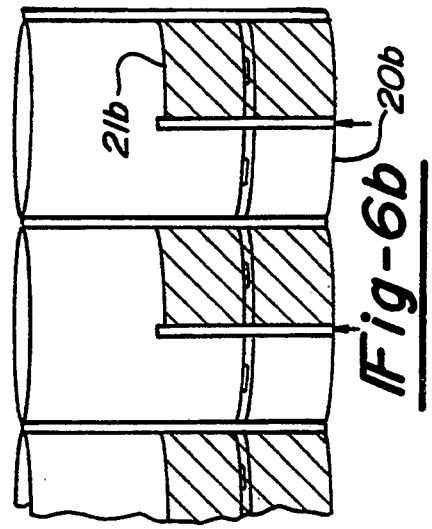
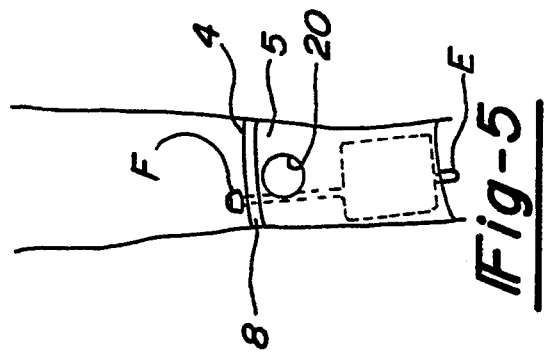
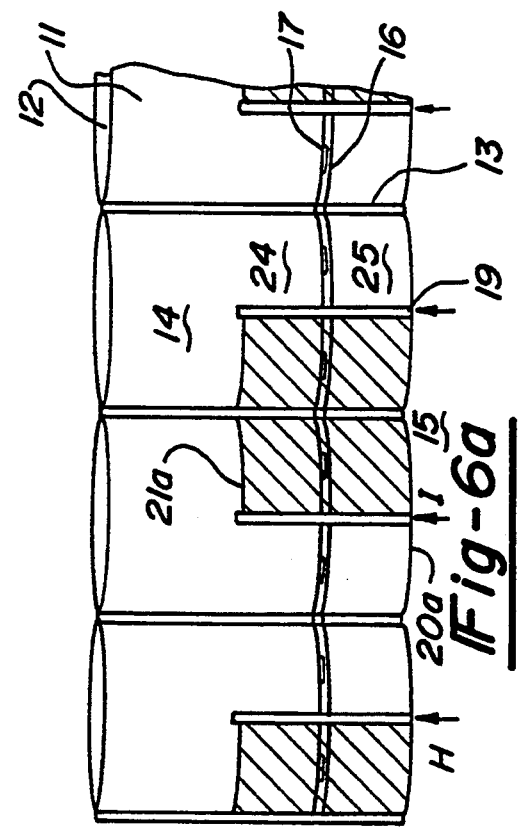
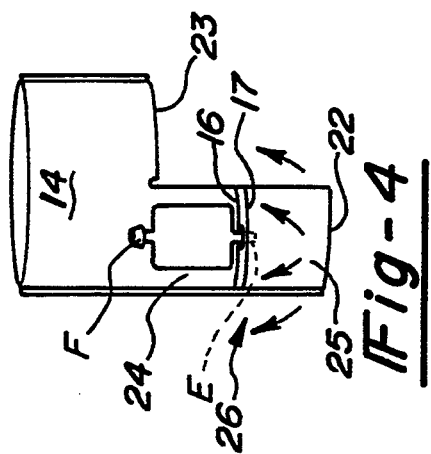

5,375,265

HOLDING MEANS

BACKGROUND OF THE INVENTION

The invention relates to an apparatus for holding a urine bag on the leg of a user, especially on the thigh. Relevant art urine bags generally include a two-layer plastic material which is continuously bonded around its edges. The top of the bag includes an inlet with a plug-on cone for discharge of a condom urinal. The bottom of the bag has an outlet with a closable valve opening. Openings or eyes are provided at the upper and lower bonded edges of the bags. Velcro strips are pulled through the openings to fix the bag in position around the thigh and secure the strips to each other at their ends. These strips unpleasantly cut into the thigh. Also, by utilizing similar strips positioned and closed around the hip of the user, with a suspended urine bag, the bag may again be held at thigh level. The unpleasant cutting effect is the same. In both cases, the securing method is not only uncomfortable, but also involves the risk of impairing blood circulation.

SUMMARY OF THE INVENTION

It is an object of the present invention to provide an apparatus for holding a urine bag on the thigh of a user. The apparatus is easy and inexpensive to produce and it also improves the wearing comfort.

The objective is achieved by providing a hose with a first knitted hose part which may be pulled over the leg, a second knitted hose part of the same diameter which, via a continuous connecting region, is connected to the said first knitted hose part. The second part is folded upwardly onto the first knitted hose part to secure the urine bag in place. Also, a separating slit, in the connecting region, enables passage of an outlet of the urine bag when the knitted hose regions are in a folded condition. The knitted hose material is very inexpensive to produce and eliminates the above problem of attaching connecting means to the urine bag. Also, the material has the advantage of distributing the elastic holding forces over a large area, as a result of which the risk of impaired circulation is greatly reduced.

The knitted hose in accordance with the invention, with both adjoining parts, is pulled over the leg. The urine bag is loosely positioned onto the upper knitted hose part of the hose. The lower knitted hose part is then folded over the upper knitted hose part while enclosing the urine bag positioned therebetween. The bag discharge valve is passed through the separating region in the connecting region. In this advantageous way, it is possible to prevent any direct contact between the plastic material and the skin of the leg which could be unpleasant when wearing the urine bag.

In order to reduce the elastic tension of the knitted hose parts on the leg, especially the thigh, and not to restrict the through-flow through the urine bag, only the first upper knitted hose part is knitted with a higher percentage of elastic threads. This part achieves the actual holding effect on the thigh. The lower, externally positioned knitted hose part is produced with fewer or no elastic threads because its only function is to prevent the urine bag from folding over or slipping. The second part does not have to accommodate its weight via friction forces. To prevent the lower knitted hose part positioned on the outside of the urine bag from folding over, it may be provided with a narrow end band with an increased elastic tension.

Additionally or alternatively, the upper first knitted hose part positioned directly on the thigh may contain rubber-coated threads to increase the friction effect. This also reduces the necessary elastic pretension of the knitted hose parts acting on the thigh.

If the urine bag, in basically the same manner, is attached to the lower leg, it is advantageous for at least the first knitted hose part and, if necessary, for the second knitted hose part to be provided with a slit which may be made to be positioned on the knee cap. Such a suspending method provides additional holding forces.

According to a second advantageous embodiment, the upper knitted hose part may form part of the leg of a pair of trousers. The trousers preferably include two legs of different lengths. With such an embodiment, the weight of the urine bag held in the same way by the upper and lower knitted hose part is accommodated via the trouser surface. In this case, there is no need to provide a greater percentage of elastic thread in the region of the upper knitted hose part. Such trousers may be designed in such a way that they include only one specially designed leg. The leg is formed of the first upper knitted hose part, with the urine bag positioned thereon and with the second lower knitted hose part being folded thereover. Thus, it is possible to design the second leg so as to be much shorter. However, it is also possible to design the second leg to be the same length as the two knitted hose parts in the folded condition.

To facilitate identification of the separating region to enable passage of the outlet, the connecting region between the two knitted hose parts has at least one marking thread of a contrasting color. Thus, the separating slit for passing through the discharge valve may be easily located. Further, the connecting region may consist of loosely knitted threads which facilitate folding in this region.

Furthermore, it is the object of the invention to provide a particularly simple and cost-effective method of producing the holding apparatus in accordance with the invention. In the case of the holding apparatus in accordance with the first embodiment, the objective is achieved by continuously knitting, in two layers (in a double section knitting manner), the knitted hose parts transversely to the longitudinal axis of the knitted hose parts. Seams are formed in the two layers at substantially equal distances with respect to each other, in that, the layers are knitted to each other across the entire width of the layers. A separating slit is provided transverse to the longitudinal axis of the knitted hose parts in one of the two layers in a connecting region between the two knitted hose parts. A separating or cutting operation is carried out along the seams to form individual holding apparatus. The method in accordance with the invention ensures that by separating individual knitted hose parts, completely finished holding apparatus in accordance with the invention are available. These parts are produced in a cost efficient manner. Instead of the separating operation referred to here, it is also possible to carry out a preseparating operation which facilitates packing of the interconnected knitted hose parts and permits final separation by tearing on the part of the user.

A method of producing holding apparatus according to the second embodiment includes continuously knitting the trousers, in pairs, in two layers in a double section knitting manner. The trousers are moved in a direction transversely to the longitudinal axis of the legs of the trousers. Seams are formed between the two layers by knitting one to the other at substantially equal distances with respect to each other. Each second seam extends across the entire width of the layers. Each seam positioned therebetween, in parallel thereto and at the same distance from the former, has only a central partial region positioned symmetrically relative to the side edges of the layers. Congruent separating slits are formed extending in both layers from the ends of the latter seam perpendicular to the legs as far as the former seam. A further short separating region is provided in one of the layers perpendicular to the direction of the legs. The material is separated at the seams into individual pairs of trousers which are separated from one another. This method, too, leads to holding apparatus which do not require any further processing and which, because of the continuous knitting technology is produced cost-effectively.

From the following detailed description taken in conjunction with the accompanying drawings and subjoined claims, other objects and advantages of the present invention will become apparent to those skilled in the art.

BRIEF DESCRIPTION OF THE DRAWINGS

Preferred embodiments of the invention are illustrated in the drawings wherein

FIG. 1 is a plan view of multiple holding apparatus being produced in a first embodiment of the invention.

FIG. 2a is an elevational view of the holding apparatus in the embodiment according to FIG. 1 in an unfolded position.

FIG. 2b is an elevational view like FIG. 2a with the holding apparatus in a folded position.

FIG. 3a is a plan view of a multiple holding apparatus being produced in a second embodiment of the invention.

FIG. 3b is a plan view like FIG. 3a of a variation of producing the holding apparatus.

FIG. 4 is an elevational view of the holding apparatus according to FIG. 3 in an unfolded position.

FIG. 5 is an elevational view of a holding apparatus in a folded position in accordance with another embodiment of the present invention.

FIG. 6a is a plan view of a holding apparatus produced in a third embodiment of the invention.

FIG. 6b is a plane view like FIG. 6a of a variation of producing the holding apparatus.

FIG. 7 is an elevational view of the holding apparatus according to FIG. 6 in an unfolded position.

DETAILED DESCRIPTION OF THE PREFERRED EMBODIMENTS

FIG. 1 shows an upper layer 1 and a lower layer 2 of a double-section knitted width of material. At desired distances, the layers i and 2 are knitted with each other in a direction transverse to the direction of production, indicated by the arrow A, to form seams 3. When separating the material along these seams 3, along the arrows B, individual hose products are obtained which include a first upper knitted hose part 4 and a second lower knitted hose part 5. The upper hose part 4 may have an increased percentage of elastic threads. Between the two parts 4 and 5 there is a connecting region 6 which may include threads knitted in a special way, e.g. loosely knitted threads. Preferably, the connecting region 6, in the upper layer 1 only, has at least one contrasting color marking thread which helps to identify the position of separating slits 7. Along the edges of the lower knitted hose part 5 there may be a band regions 8 having an increased percentage of elastic threads.

In FIG. 2, the holding apparatus includes an upper knitted hose part 4 and a lower knitted hose part 5 pulled over a leg C as far as the thigh. A urine bag D is positioned in the region of the upper knitted hose part 4. The bag's lower discharge valve E has already been passed through a separating slit 7. In accordance with the arrows shown in FIG. 2a, the lower second knitted hose part 5 is folded over the upper knitted hose part 4. The urine bag is secured in the holding apparatus as shown in FIG. 2b. The bag's connecting cone F and discharge valve E are exposed, with the urine bag held between the knitted hose parts 4 and 5.

In FIG. 3, an upper layer 11 and a lower layer 12 of a double section knitted width are knitted together at first seams 13 along the entire width of the material. Between the seams 13 there is provided a second seam 19 which is at the same distance from the former and extends in parallel thereto. The second seams 19 only include part of the width of the layers knitted together and are symmetrical relative to the side edges.

The direction of production of the width of material is indicated by the arrow G. Between the seams 13 and 19 first separating slits 20a, 21a, 20b, 21b are provided in both layers 11 and 12. The slits 20 and 21 extend in the longitudinal direction with respect to the width of material. Furthermore, at least one of the layers is provided with a marking strip 16, preferably in a contrasting color which comprises short separating slits 17 in only one layer. Arrows H, I indicate that along the seams 13 and 19 central separation is to take place. At the seams 19, the separation must not extend beyond the two ends of the seam. FIGS. 3a and 3b differ in respect of the position of the separating slits 20 and 21 between the individual separating regions 13.

The position of the seams 13 and 19 and the position of the separating slits 20 and 21 indicate the existence of trousers 14 and 15 as semi-finished products between two seams 13. Each of the pairs of trousers 14 and 15 include a first knitted hose part 24 and a second knitted hose part 25 between which a separating region with slits 17 is provided in only one of the layers 11.

A method of producing the trousers is as follows, Continuously knitting trousers, with legs, in pairs in two layers in a double section knitting manner. Making the trousers in a direction transverse to a longitudinal axis of the legs. Forming at least two seams in the two layers such that the layers are knitted with each other and forming subsequent seams at substantially equal distances with respect to one another with each of the at least two seams and subsequent seams extending widthwise across the layers. Forming an in-between seam between the at least two seams and subsequent seams. Each in-between seam is in parallel thereto and at the same distance from the former. The in-between seams are in a central partial region positioned symmetrically relative to side edges of the two layers. Forming congruent separating slits in both layers extending from the at least two seams and subsequent seams perpendicular to the legs extending to the in-between seams. Forming a short separating slit in one of the layers perpendicularly to the direction of the legs. Separating the seams and forming individual pairs of trousers separated from one another.

FIG. 4 shows a pair of trousers 14 comprising a first leg opening 22 produced by the separating slit 20, and a second leg opening 23 produced by the separating slit 21. The leg opening 22 forms the lower end of a longer leg 26. The urine bag D is placed on the upper portion of the leg part 26, with its discharge valve E already having been passed through a separating region slit 17 in the marking region 16. As indicated by the arrows, the lower knitted hose part 25 of the leg 26 is folded over the upper knitted hose part 24 in a manner similar to that shown in FIG. 2b. In this case, the elastic band has been eliminated.

FIG. 5 shows another embodiment of the invention. In this case, the holding apparatus is like that in FIGS. 2a and 2b. However, the first and second hose parts include an aperture or slit 20 to enable positioning about the knee cap to further suspend and hold the apparatus onto the leg.

FIGS. 6 and 7 illustrate a process of forming trousers similar to FIGS. 3 and 4 and thus the same reference numerals have been used. However, in FIGS. 6a and 6b the in between seam extends half way and only a single pair of trousers are formed with a portion of scrap material.

A method of producing trousers is as follows. Continuously knitting trousers, with legs, in pairs in two layers in a double section knitting manner. Making the trousers in a direction transverse to a longitudinal axis of the legs. Forming at least two seams in the two layers in that the layers are knitted with each other and forming subsequent seams at substantially equal distances with respect to one another with each of the at least two seams and subsequent seams extending widthwise across the layers. Forming an in-between seam between the at least two seams and subsequent seams. Each in-between seam is in parallel thereto and at the same distance from the former. The in-between seams start from side edges of the two layers and extend half the width of the layers. The in-between seams have ends, Forming congruent separating slits in both layers extending from the ends of the in-between seams perpendicular to the legs extending to one of the at least two seams and subsequent seams. Forming a short separating slit in one of the layers perpendicularly to the direction of the legs. Separating the seams and forming individual pairs of trousers separated from one another.

While the above detailed description describes the preferred embodiment of the present invention, the invention is susceptible to modification, variation, and alteration without deviating from the scope and fair meaning of the subjoined claims.

I claim:

1. An apparatus for holding a urine bag on the leg of a user, comprising:
   a first knitted hose part of a diameter sufficient to completely encircle a portion of a wearer's leg, said first knitted hose part defining a longitudinal axis and which may be pulled over the leg;
   a second knitted hose part of the same diameter connected along a line transverse to the longitudinal axis in an unfolded position with said first knitted hose part via a continuous connecting region for the purpose of securing a urine bag, said second hose part being foldable over onto and nonattached to the first knitted hose part apart from said connecting region; and
   separating slit in the connecting region for permitting the passage of an outlet of the urine bag when the first and second knitted hose regions are in a folded condition.

2. The holding apparatus according to claim 1 wherein said first knitted hose part is comprised of a knitted fabric with a higher percentage of elastic thread.

3. The holding apparatus according to claim 1 wherein at least said first knitted hose part includes a slit for being fixed to the knee cap of the user when the urine bag is arranged at the lower leg of the user.

4. The holding apparatus according to claim 1 wherein said first knitted hose part forms part of a leg of a pair of trousers.

5. The holding apparatus according to claim 1 wherein said connecting region is comprised of loosely knitted threads.

6. The holding apparatus according to claim 1 wherein at least one marking thread of a contrasting color is inserted into the connecting region.

7. The holding apparatus according to claim 1 wherein a narrow holding band is provided at the free end of the second knitted hose part.

8. A method of producing a holding apparatus for a urine bag comprising:
   continuously knitting hoses with a first part and second part defining a longitudinal axis and connected along a line transverse to said longitudinal axis defined at said first part via a continuous connecting region in two layers in a double section knitting manner making the hoses in a direction transverse to longitudinal axis of the hoses;
   forming seams in the two layers at substantially equal distances with respect to one another in that the layers are knitted widthwise with one another across the layers;
   forming a separating slit in one of the two layers in the connecting region;
   separating said layers along said seams; and
   providing one or more individual hose apparatus for holding a urine bag.

9. A method according to claim 8 further comprising providing a slit for enabling attachment to one of the user's knee caps at a distance from the separating slit in the first knitted hose part.

10. A method of producing a holding apparatus for a urine bag comprising:
    continuously knitting trousers, with legs, in pairs in two layers in a double section knitting manner;
    making the trousers in a direction transverse to a longitudinal axis of the legs;
    forming at least two seams in the two layers such that the layers are knitted with each other and forming subsequent seams at substantially equal distances with respect to one another with each of said at least two seams and subsequent seams extending widthwise across the layers;
    forming an in-between seam between said at least two seams and subsequent seams, each in-between seam , in parallel thereto and at the same distance from the former, with said in-between seams in a central partial region positioned symmetrically relative to side edges of the two layers;
    forming congruent separating slits in both layers extending from the at least two seams and subsequent seams perpendicular to the legs extending to the in-between seams;
    forming a short separating slit in one of the layers perpendicularly to the direction of the legs; and separating the seams and forming individual pairs of trousers separated from one another.

11. A method of producing a holding apparatus for a urine bag comprising:

continuously knitting trousers, with legs, in pairs in two layers in a double section knitting manner;

making the trousers in a direction transverse to a longitudinal axis of the legs;

forming at least two seams in the two layers in that the layers are knitted with each other and forming subsequent seams at substantially equal distances with respect to one another with each of said at least two seams and subsequent seams extending widthwise across the layers;

forming an in-between seam between said at least two seams and subsequent seams, each in-between seam, in parallel thereto and at the same distance from the former, with said in-between seams starting from side edges of the two layers and extending half the width of the layers; said in between seams having ends;

forming congruent separating slits in both layers extending from the ends of the in-between seams perpendicular to the legs extending to one of the at least two seams and subsequent seams;

forming a short separating slit in one of the layers perpendicularly to the direction of the legs; and separating the seams and forming individual pairs of trousers separated from one another.

* * * * *